US00PP15499P2

(12) United States Plant Patent
Olesen et al.

(10) Patent No.: US PP15,499 P2
(45) Date of Patent: Jan. 25, 2005

(54) ROSE PLANT NAMED 'POULAC008'

(50) Latin Name: *Rosa hybrida*
Varietal Denomination: POULac008

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,153

(22) Filed: Dec. 16, 2003

(51) Int. Cl.[7] ..... A01H 5/00
(52) U.S. Cl. ..... Plt./145
(58) Field of Search ..... Plt./145, 134, 104

*Primary Examiner*—Anne Marie Grunberg
*Assistant Examiner*—June Hwu

(57) ABSTRACT

A new garden rose plant of the compact floribunda class which has abundant, yellow flowers and attractive foliage. This new and distinct variety has shown to be uniform and stable in the resulting generations from asexual propagation.

1 Drawing Sheet

Botanical classification: *Rosa hybrida.*
Variety denomination: 'POULac008'.

SUMMARY OF THE INVENTION

The present invention constitutes a new and distinct variety of garden rose plant which originated from a controlled crossing between the female parent, an unnamed plant, and the male parent 'POULjoey', described and illustrated in U.S. Plant Pat. No. 11,598 issued Oct. 24, 2000. The two parents were crossed during the summer of 1995 and the resulting seeds were planted in a controlled environment in Fredensborg, Denmark. The new variety is named 'POULac008'.

The new variety may be distinguished from its female unnamed seed parent by the following combination of characteristics:

1. While the seed parent has an average flower diameter of 50 mm to 60 mm. 'POULac008' has a 65 mm to 75 mm flower diameter.
2. While the seed parent has a yellow-orange general tonality, 'POULac008' is yellow.

The new variety may be distinguished from its male pollen parent, 'POULjoey' by the following combination of characteristics:

1. While the seed parent 'POULjoey' is a bronze-colored 'POULac008' is yellow.
2. While the seed parent 'POULjoey' has a petal color of Orange Group 28C and Red Group 39B–C, the same of 'POULac008' is Yellow Group 12A.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Disease resistance.

This combination of qualities is not present in previously available commercial cultivars of this type, known to the inventors, and distinguish 'POULac008' from all other varieties of which we are aware.

As part of their rose development program, L. Pernille Olesen and Mogens N. Olesen germinated the seeds from the aforementioned hybridization during winter of 1995 and conducted evaluations on the resulting seedlings in a controlled environment in Fredensborg, Denmark.

'POULac008' was selected in the spring 1996 by the inventors as a single plant from the progeny of the aforementioned hybridization.

Asexual reproduction of 'POULac008' by traditional budding and rooted cuttings was first done by L. Pernille and Mogens N. Olesen in their nursery in Fredensborg, Denmark in July, 1996. This initial and other subsequent asexual propagations conducted in controlled environments have demonstrated that the characteristics of 'POULac008' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac008'.

Specifically illustrated in the drawing:

FIG. 1.2; Sepals, receptacle, and peduncle;

FIG. 1.3; Flower petals, detached;

FIG. 1.4; Bare stem exhibiting thorns;

FIG. 1.5; Mature Leaf.

DETAILED DESCRIPTION OF THE VARIETY

Figures 1A, 1B, 1C, 1D, 1E, 1F:
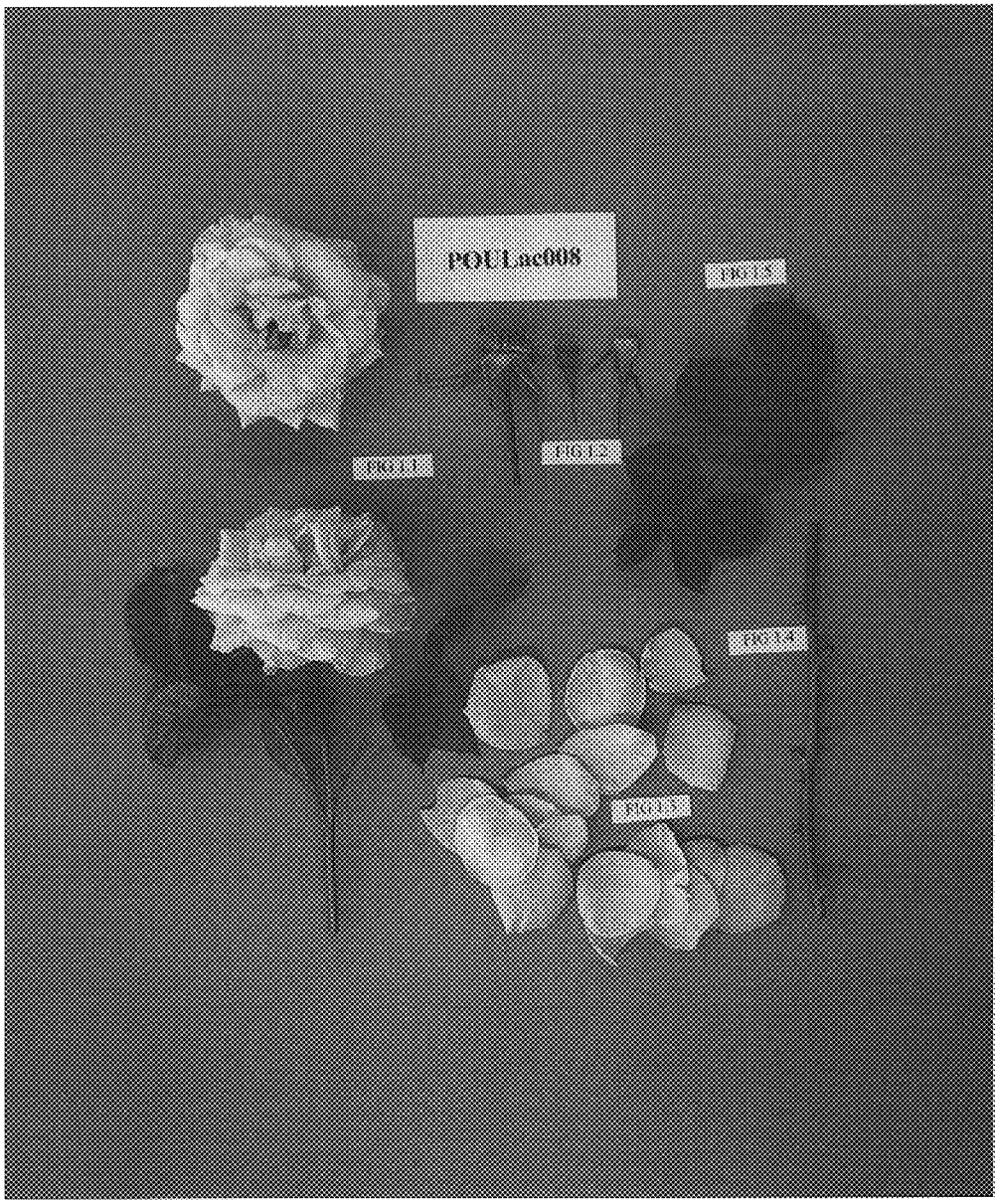
FIG. 1.1; Open flower, stem showing open flower, branching, and the attachment of leaves, buds, and peduncles.

The following is a description of 'POULac008', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULsiana', a rose variety from the same inventors described and illustrated in U.S. Plant Pat. No. 11,638 dated Nov. 21, 2000, are compared to 'POULac008' in Chart 1.

CHART 1

| | 'POULac008' | 'POULsiana' |
|---|---|---|
| Average diameter of flower bloom when open | 65 mm to 75 mm. | 55 mm to 60 mm. |
| Color upon opening, petals, upper surface. | Yellow Group 7A. | Yellow Group 12B to 12C with occasional intonations of Yellow Group 11C. |
| Leaf size. | 30 mm to 45 mm (1) × 20 mm to 30 mm (w). | 85 mm to 90 mm (1) × 60 mm (w). |

Parents:

*Female seed parent.*—Unnamed plant.

*Male pollen parent.*—'POULjoey'.

FLOWER AND FLOWER BUD

Blooming habit: Continuous.

Flower bud:

*Color.*—As sepals unfold, petals are Yellow Group 8B in color. Size: Length from base of the receptacle to end of bud is 20 mm. 15 mm wide.

*Sepals.*—Upper Surface: Color: Yellow-Green Group 146A to 146B. Texture: Moderately pubescent. Lower Surface: Color: Yellow Green Group 146A to 146C. Anthocyanic pigments the color of Greyed-Purple Group 187C observed in the center and on the foliaceous appendages. Texture: Smooth with many stipitate glands. Sepal Shape: Sepal apex is cirrhose. Base is flat at union with receptacle. Sepal Margin: Margins have strong to medium foliaceous appendages on three of the five sepals. Size: 30 mm to 35 mm (l) by 8 mm to 10 mm (w).

*Receptacle.*—Surface Texture: Smooth, glabrous and glaucous. Shape: Urn-shaped. Size: 7 mm to 8 mm (h)×8 mm to 10 mm (w). Color: Yellow-Green Group 144A to 144B. Anthocyanin: Greyed-Purple Group 187B to 187C.

*Peduncle.*—Surface: Rough. Prickles and stipitate glands observed. Length: 45 mm to 50 mm. Diameter: 2 mm. Color: Yellow-Green Group 144A. Anthocyanic pigments the color of Greyed Orange 174A observed.

*Borne.*—9 flower buds per stem on average.

Flower bloom:

*Fragrance.*—Light and floral.

*Duration.*—The blooms have a duration on the plant of approximately 7 to 10 days. Afterwards, petals fall cleanly away from plant.

*Size.*—Flower diameter is 65 mm to 70 mm when open.

*Form.*—General shape is an open cup with outer petals reflexing strongly.

*Shape of flower when viewed from the side.*—Upon opening; Upper part: Flattened convex. Lower part: Concave. Open flower; Upper part: Flattened convex. Lower part: Concave.

*Petalage.*—70 to 75 petals under normal conditions with 15 petaloids.

Flower color:

*Upon opening.*—Outermost petals: Outer side: Yellow Group 12B to 12C with occasional intonations of Yellow Group 11C. Inner side: Yellow Group 12A. Innermost petals: Outer side: Yellow Group 12B to 12C. Inner side: Yellow Group 12A.

*Upon opening, basal petal spots.*—Outermost petals: Outer side: Yellow Group 12B to 12C. Inner side: Yellow Group 12A. Innermost petals: Outer side: Yellow Group 12B to 12C. Inner side: Yellow Group 12A.

*After opening.*—Outermost petals: Yellow Group 12B to 12C with occasional intonations of Yellow Group 11C. Inner side: Yellow Group 12A. Innermost petals: Outer side: Yellow Group 12B to 12C. Inner side: Yellow Group 12A. After opening, no distinctive coloration at petal base observed.

General tonality: On open flower Yellow Group 12A. No change in the general tonality at the end of the $10^{th}$ day. Afterwards, general tonality is Yellow Group 11A to 11C.

Petals:

*Petal reflex.*—Medium to strong.

*Margin.*—Entire, with point in center of margin.

*Shape.*—Apex: Round. Base: Acute.

*Size.*—35 mm to 40 mm (l)×30 mm to 35 mm (w).

*Texture.*—Smooth.

*Thickness.*—Thin.

*Arrangement.*—Not Formal.

Petaloids:

*Quantity.*—15.

*Color.*—Upper surface is Yellow Group 12A. Lower surface is Yellow Group 10A to 10B.

*Size.*—15 mm to 20 mm (l)×5 mm to 11 mm (w).

Reproductive organs:

*Pollen.*—None observed.

*Anthers.*—Size: 1 mm to 3 mm long. Color: Brown Group 200A to 200B. Quantity: 160 (actual count).

*Filaments.*—Color: Yellow-Orange Group 17C. Length: 5 mm to 10 mm.

*Stigmas.*—Inferior in location to anthers. Color: Greyed-Orange Group 163A.

*Styles.*—Color: Yellow-Green Group 144D. Length: 6 mm. Other intonations: At top of styles and extending into the anthers with streaks of Yellow-Green Group 144B.

*Hips.*—None observed in the field nursery in Jackson County Oreg.

PLANT

Plant growth: Moderate, upright to bushy. When grown as a budded field grown plant on *Rosa multiflora* understock, the height of the plant is 40 to 60 cm and the average width is 40 cm.

Stems:

*Color.*—Young wood: Yellow-Green Group 144A. Older wood: Yellow-Green Group 144A.

*Surface texture.*—Young wood: Smooth. Older wood: Smooth.

Thorns:

*Incidence.*—6 thorns per 10 cm of stem.

*Size.*—Average length: 6 mm.

*Color.*—Juvenile thorns are Greyed-Purple Group 181B to 181C. Mature thorns are Greyed-Yellow Group 160A.

*Shape.*—Linear to concave.

Plant foliage: Normal number of leaflets on normal leaves in middle of the stem: 5 leaflets.

*Compound leaf size.*—120 mm (l)×80 mm (w).

*Quantity.*—Average.

*Color.*—Mature foliage: Upper Leaf Surface: Yellow-Green Group 146A. Lower Leaf Surface: Yellow-Green Group 146C. Juvenile foliage: Upper Leaf Surface: Yellow-Green Group 146A. Lower Leaf Surface: Yellow-Green Group 146C. Anthocyanin: Location: New growth of top leaves, rachis, petiole and stipule. Color: Greyed-Purple Group 187B observed.

Plant leaves and leaflets:

*Stipules.*—Size: 26 mm in length. Color: Yellow-Green Group 144A. Shape: Linear, slightly broad based with outward extending apecies. Margins: Finely serrated with few stipitate glands.

*Petiole.*—Length: 25 mm to 30 mm. Color: Yellow-Green Group 144A. Underneath: Yellow-Green Group 144A. Few stipitate glands and thorns observed. Margins: Stipitate glands present.

*Rachis.*—Color: Yellow-Green Group 144A. Anthocyanin: Greyed-Purple Group 183A to 183D in between top margins. Underneath: Yellow-Green Group 144A. Thorns on the underside.

*Leaflet.*—Size: 30 to 45 mm (l)×20 to 30 mm (w). Edge: Serrated. Shape: Ovate to round with cuspidate apex and a round base. Texture: Smooth. Arrangement: Odd pinnate. Venation: Reticulate. Glossiness: Moderately glossy.

Disease resistance: Above average resistance to mildew, rust, black spot, and Botrytis under normal growing conditions in Jackson County, Oreg.

Cold hardiness: The variety 'POULac008' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant yellow, disease resistance, and extended period of bloom.

* * * * *

POL Lac008